United States Patent
Bhatt et al.

(10) Patent No.: US 6,284,225 B1
(45) Date of Patent: Sep. 4, 2001

(54) PROPELLANT COMPOSITIONS COMPRISING A HYDROFLUOROCARBON AND A HYDROCARBON

(75) Inventors: Darshna Bhatt, Schaumburg; Arun Nandagiri, Libertyville; Jitendra Patel, Fox River Grove, all of IL (US)

(73) Assignee: Helene Curtis, Inc., Chicago, IL (US)

( * ) Notice: Subject to any disclaimer, the term of this patent is extended or adjusted under 35 U.S.C. 154(b) by 0 days.

(21) Appl. No.: 09/115,533

(22) Filed: Jul. 15, 1998

Related U.S. Application Data

(60) Provisional application No. 60/060,248, filed on Sep. 29, 1997.

(51) Int. Cl.$^7$ ................................................ A61K 7/11
(52) U.S. Cl. ................ 424/45; 424/47; 424/DIG. 1; 424/DIG. 2; 424/70.11; 514/945
(58) Field of Search ................ 424/45, 47, DIG. 1, 424/DIG. 2, 70.11; 514/945

(56) References Cited

U.S. PATENT DOCUMENTS

| | | | |
|---|---|---|---|
| 4,847,068 | * | 7/1989 | Dole et al. . |
| 4,847,076 | | 7/1989 | Deshpande et al. . |
| 5,609,857 | | 3/1997 | Chandran et al. . |
| 5,676,931 | * | 10/1997 | Adjei et al. ........................ 424/45 |

OTHER PUBLICATIONS

Manufacturing Chemist 66(10), Oct. 95, p. 57.*

* cited by examiner

*Primary Examiner*—Raj Bawa
(74) *Attorney, Agent, or Firm*—Matthew Boxer

(57) ABSTRACT

Foaming propellant compositions for use in hair mousse compositions described. These compositions contain hydrofluorocarbon 152A and a suitable hydrocarbon in a ratio of about 30 to 70; to about 50 to 50; more preferably about 40 to 60. These compositions comprise the hydrofluorocarbon 152A; and a hydrocarbon, selected from the group consisting of propane, isobutane, and n-butane in the above recited ratios. The above propellant mixture is about 4 to 9 wt. % of total foaming, hair care composition.

4 Claims, No Drawings

PROPELLANT COMPOSITIONS COMPRISING A HYDROFLUOROCARBON AND A HYDROCARBON

This application claims benefit of provisional No. 60/060,248 filed Sep. 29, 1997.

FIELD OF THE INVENTION

This invention relates to the development of superior foam characteristics of foaming propellant compositions such as mousse products

BACKGROUND OF THE INVENTION

In the formulation of foaming aerosol products, an essential component is the propellant which is used to dispense the liquid concentrate. In manufacturing, the liquid concentrate is first filled into the aerosol can which is sealed with a valve cup and then the propellant is introduced via pressure filling. It is also possible to do under the cup filling where the propellant is filled and the valve cup sealed in one step. Commonly used propellants in the formulation of personal care products can be classified into two major groups: Compressed gases and Liquefied propellants.

Compressed Gases

Examples of compressed gases are nitrogen, carbondioxide, etc., which remain as gases in the aerosol can. Depending on the type of concentrate used, they can be partially solubilized in the liquid concentrate. The pressure that results from such a product can be controlled by the amount of propellant that is solubilized in the liquid concentrate and what is left in the head space. Compressed gases are not widely used in personal care products since the pressure drops over the life of the can when it is being used resulting in different spray characteristics, lower spray rates and poorer foam quality. However the advantage of compressed gases is that they are inexpensive compared to liquefied propellants.

Liquefied Propellants

They are so called because they are gases under normal temperature and pressure but become liquids under higher atmospheric pressure. The advantage of using liquefied propellants is that they maintain a constant pressure throughout the life of the can by converting from a liquid state to a gaseous state as the can is depleted. This provides the user with a product that does not vary too much in its properties. Commonly used liquefied propellants are hydrocarbons, hydrofluorocarbons and dimethylether. Fluorocarbons were the most widely used propellants up until the mid 1970's when their use was restricted because they were alleged to damage the ozone layer. Hydrocarbons are now the propellant of choice because they are readily available and are less expensive than hydrofluorocarbons. Hydrocarbons used in the personal care industry are usually mixtures of Isobutane, n-butane and propane. These three are blended to give the desired pressure. For example, hydrocarbon A-46 is a mixture of 15.1% by weight of propane and 84.9% by weight of isobutane blended to give 46 psig pressure at 70 F. If lower pressures are desired, then the propellants are used as is. For example, n-butane has a pressure of 17 psig at 70 F. and Isobutane has a pressure of 31 psig at 70 F. which can be used without blending.

Hydrofluorocarbons belong in the liquefied propellant group but are not widely used because of their expense. The most commonly used hydrofluorocarbon is Dymel 152A manufactured by Dupont. Dymel 152A has a pressure of 62 psig at 70 F. which makes it desirable for a number of applications. In hair sprays for example, this pressure is lowered by its solubility in the alcohol base which gives an even soft spray and in hair mousses, it is used to give a rich dense foam. Dymel 152A is also denser than hydrocarbons which is an advantage when filling cans to a desired weight.

Dimethyl ether is another good propellant. Unlike hydrocarbons, it is extremely soluble in water. It is also reasonably priced and as a result has found its place in water based hair spray formulations. Its use in mousses as a sole propellant is limited due to high solubility.

Formulation Considerations

In the formulation of mousse products, the choice and amount of propellant used plays a major role in the quality of the foam produced. The two propellants that are currently used in the U.S. are Dymel 152A ( known as Dymel 152 and 152A, available from E. I. Dupont, Wilmington, Del.) and Hydrocarbon A-17(n-butane). Formulation parameters that make these two propellants attractive are: Pressure of the finished product, which should be such that the amount dispensed is in an acceptable range and the product can be packaged in a suitable can. The density of the formulation which determines how much weight percent of the active that can be dispensed each time. The quality of the foam is also a function of the type of propellant used—Dymel 152A gives a rich dense foam while hydrocarbon foams are more airy. The amount of propellant used in hair mousse formulations is typically between 4–9% by weight. At propellant levels higher than 9% by weight, the foam produced is dry whereas at lower levels below 4% the foam is not dense and runny.

Although other ingredients in the formulation also play a role in the quality of the foam especially the level and type of surfactant used, it could generally be stated that Dymel 152A as a propellant has advantages over hydrocarbon dispensed products in producing a rich foam, and a dense foam which carries with it a higher active level. On the other hand, its disadvantages are is its cost and the resultant product has a higher pressure requiring it to be packaged in a more expensive can to meet department of transportation regulations.

The problem that this invention has attempted to solve is how to get all of the advantages of the Dymel 152A propelled product to combine with all of the advantages of the hydrocarbon while keeping the cost of the finished product and the can to be at its lowest level.

In brief, the present invention is directed towards producing a mousse product composition that is dispensed with a particular ratio of Dymel/hydrocarbon propellant to maximize its foam quality while minimizing the cost of the product and the can it is packaged in.

Accordingly, it is an object of this invention to produce a foam that is rich in quality but yet at the same time is less expensive and can be packaged acceptably without using an expensive quality can.

The invention provides a propellant composition having low vapor pressure, good foaming properties.

A propellant composition that is lower in vapor pressure is safer to use and handle and can be dispensed from lighter, less expensive containers.

Another measure of propellant is the foam which it produces. A preferred foam will be creamy feeling and looking and will have a slippery feel. An added advantage is if the propellant can produce a shiny foam. These characteristics are all achieved by the present invention.

SUMMARY OF THE INVENTION

The present invention pertains to foaming propellant compositions for use in hair mousse compositions containing hydrofluorocarbon 152A and a suitable hydrocarbon in a ratio of about 30 to 70; to about 50 to 50; more preferably about 40 to 60.

DETAILED DESCRIPTION OF THE INVENTION

The propellant compositions of the invention comprise 152A and a suitable hydrocarbon in ratios that range from about 30:70 to 50:50; more preferably about 40:60.

Suitable hydrocarbons include propane, isobutane, n-butane and mixtures thereof. Most preferably, the hydrocarbon employed is n-butane.

Compositions of the invention preferably contain a mixture of anionic/nonionic surfactant/emulsifiers. The compositions of the invention may also contain cationic surfactants as long as the cationic surfactants are compatible with any anionics that may be present. The present invention relates to alcoholic and non-alcoholic foaming propellant compositions.

Compositions of the invention may contain a surfactant or emulsifier such as a mild anionic surfactant or amphoteric surfactant.

Preferred mild anionic and amphoteric surfactants used in this invention include: alkyl glyceryl ether sulfonate (AGS), anionic acyl sarcosinates, methyl acyl taurates, N-acyl glutamates, acyl isethionates, alkyl sulfosuccinate, alkyl phosphate ester, ethoxylated alkyl phosphate esters, alkyl sulfates, protein condensates, mixtures of ethoxylated alkyl sulfates and alkyl amine oxides, betaines, sultaines, and mixtures thereof. Alkyl chains for these surfactants are $C_8$–$C_{22}$, preferably $C_{10}$–$C_{18}$.

Emulsifiers may be added to the formula to improve the phase stability of the concentrate, however, they are not necessary for a stable aerosol product that would be shaken before use.

Emulsifiers can be selected from the group consisting of polyethoxylated or propoxylated $C_8$–$C_{22}$ fatty acids, alcohols or glycols having less than about 30 moles of ethylene oxide per mole of fatty acid, ethoxylated esters, unethoxylated sugar esters, polyoxyethylene fatty ether phosphates, fatty acid amides, phospholipids, polypropoxylated fatty ethers, acyl lactylates, polyethoxylated poly (oxypropylene) glycols, polypropoxylated poly (oxyethylene) glycols, poly (oxyethylene) poly (oxypropylene) ethylene di-amines, and mixtures thereof.

Examples of such emulsifiers include polyoxyethylene (8) stearate, myristyl ethoxy (3) palmitate, methyl glucoside sequestrate, sucrose distearate, sucrose laurate, sorbitan monolaurate, polyoxyethylene (3) oleyl ether phosphate, polyoxyethylene (10) oleyl ether phosphate, lauric diethanolamide, stearic monoethanolamide, lecithin, lanolin alcohol propoxylates, sodium stearol-2-lactylate, calcium stearoyl-2-lactylate and the Pluronics offered by BASF Wyandotte.

Perfumes may be used in such products, generally at a level of about 0.1% to about 1% of the concentrate to cover the base odor. Colorants may also be used. Opacifiers, e.g., ethylene glycol distearate, polystyrene latex, generally at a level of about 0.2% of the concentrate, may also be used to provide the mousse with an opaque or pearlescent appearance. Preservatives, e.g. EDTA, methyl paraben, propyl paraben, Germall 115, Kathon, generally at a level of less than 1% of the concentrate, may be incorporated in the emulsion to prevent microbiological growth.

The following examples are typical of the foaming propellant compositions of the present invention. These examples are presented for purposes of illustration only, and are not intended as a limitation on the scope of the invention as described herein.

| Ingredients | Formula A | Formula B | Formula C | Formula D |
| --- | --- | --- | --- | --- |
| Water D.I. | 90.1895 | 90.1895 | 92.0060 | 92.0060 |
| Polyurethane | 0.7065 | 0.7065 | 0.6 | 0.6 |
| Gafquat 755N | 8.6 | 8.6 | 7.0 | 7.0 |
| Sodium Cocoyl Isothionate | 0.054 | 0.054 | 0.054 | 0.054 |
| Luaramid DEA | 0.01 | 0.01 | 0.01 | 0.01 |
| Isosteareth 10 | 0.082 | 0.082 | 0.082 | 0.082 |
| Kathon CG | 0.054 | 0.054 | 0.054 | 0.054 |
| DMDM Hydantoin | 0.054 | 0.054 | 0.054 | 0.054 |
| Fragrance | 0.1 | 0.1 | 0.1 | 0.1 |
| AMP | 0.15 | 0.15 | 0.04 | 0.04 |
| Propellants | 70 dymel /30 hydrocarbon | Hydrocarbon | 70 dymel /30 hydrocarbon | 40 dymel/ 60 hydrocarbon |

Formulas A, B and C above are not within the scope of the present invention. Formula D above is within the scope of the present invention.

Formulas above were prepared using the following procedure.

Manufacturing Procedure

Take Deionized water into a clean tank. Heat the batch to 90 F. Turn agitation to high. Slowly sift Polyurethane Resin into the tank. Mix until uniformly dispersed, approximately 30 minutes. Increase the temperature to 131 F. (55 C.). When the temperature is 131 F. add AMP. Mix for 30 minutes to dissolve completely. When solution is clear add Isosteareth 10 and mix until completely dissolved (approx. 15 minutes). Turn heat off and cool the batch to 90 to 100 F. Add the following items and mix until uniform after each addition: Sodium Cocoyl Isothionate, Lauramide DEA, Gafquat 755N, Kathon CG, DMDM Hydantoin, and Fragrance.

Fill the above liquid concentrate into the aerosol can, sealed with a valve cup and then introduce the propellant via pressure fill or under the cup filling.

As has been stated an object of the invention is to produce a propellant composition which may be used in a standard strength tube (or a 2N can) rather than an expensive (2Q)can. In the table just below are listed the characteristics of the different types of cans. The cost of a "2Q" can may be 25% greater than the cost of a "2N" can. Thus the fact that the propellant foaming compositions of the present invention allow for the use of a "2N" can provide great cost savings in the manufacture of canned foamed propellant compositions of the claimed invention.

| Pressure at 130 F. | <140 psi | 140–160 psi | 160–180 psi |
|---|---|---|---|
| DOT Can Regulation (Type of can) | 2N | 2P | 2Q |
| Price | Least | Mid | High |
| Propellant | Hydrocarbon | 40/60(dymel/HC) | 70/30(dymel/HC) |
| Performance (Finished Product) | Hydrocarbon: Preferred among value brand users 40/60: Preferred among representative samples which includes premium brand user | | 70/30(dymel/HC) Preferred among representative samples which includes premium brand user |

DOT = Department of Transportation; 2N is a standard strength tube.

As has been stated, an object of the invention is to produce a mousse product with a foam that is rich in quality, but yet at the same time is less expensive and can be packaged acceptably without using an expensive quality can. In fact, a 2N type can, which is the least expensive type of can in the above table, may be used with the compositions of the invention. The type and level of emulsifiers/surfactants employed can also result in further lowering of the pressure of the final product. If the pressure of the final product is low enough, a less expensive can may be used.

It should be expected that when the percentage of 152A is decreased the quality of the foam produced will also decrease and that the creamy, slippery, shiny appearance will be replaced by the stiffer, more brittle foam produced by the hydrocarbon. However, at the 40:60 ratio, extensive market research showed that compositions of the invention were received favorably by both the value and premium brand users.

In order to determine the acceptability of various types of mousse products among users, extensive market research studies were done with hydrocarbon and 152A/hydrocarbon mousse products. Users of these products fall into two groups—those that prefer the hydrocarbon products and those that prefer the 152A/hydrocarbon products. Those that prefer the hydrocarbon products are in the value segment of the market where the price of the product is an important consideration, while those that prefer the 152A/hydrocarbon products are in the premium market segment where price is not as important as the quality of the product. Extensive market research further showed that compositions of the invention which comprised a 40:60 ratio of 152A/hydrocarbon were received favorably by both the value and the premium segment of the market, by providing a product with good foam, that was packaged in an inexpensive can.

We claim:

1. A foaming propellant composition wherein said composition is a hair mousse a) a resin;

b) a surfactant;

c) a fragrance; and d) a propellant.

2. A combination comprising a) a composition according to claim 1;

b) in a can.

3. A combination according to claim 2, wherein the can is a 2N can.

4. A method for styling hair which comprises applying to hair a composition according to claim 1.

* * * * *